(12) United States Patent
Ziegler et al.

(10) Patent No.: US 6,723,363 B2
(45) Date of Patent: Apr. 20, 2004

(54) COATING FOODS AND PHARMACEUTICALS WITH AN EDIBLE POLYMER USING CARBON DIOXIDE

(75) Inventors: Gregory R. Ziegler, State College, PA (US); Richard A. Wysk, Boalsburg, PA (US); Matthew C. Frank, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 101 days.

(21) Appl. No.: 09/941,794

(22) Filed: Aug. 30, 2001

(65) Prior Publication Data

US 2002/0045004 A1 Apr. 18, 2002

Related U.S. Application Data

(60) Provisional application No. 60/228,966, filed on Aug. 30, 2000, and provisional application No. 60/228,906, filed on Aug. 29, 2000.

(51) Int. Cl.$^7$ .................................................. A23P 1/08
(52) U.S. Cl. ...................... 426/302; 426/303; 427/2.14; 427/2.5
(58) Field of Search ................................ 426/302, 303; 427/2.14, 2.55

(56) References Cited

U.S. PATENT DOCUMENTS

| | | |
|---|---|---|
| 3,949,096 A | 4/1976 | Johnson et al. |
| 4,661,359 A | 4/1987 | Seaborne et al. |
| 4,710,228 A | 12/1987 | Seaborne et al. |
| 4,810,534 A | 3/1989 | Seaborne et al. |
| 4,923,720 A | 5/1990 | Lee et al. |
| 5,512,231 A * | 4/1996 | Thies et al. .................. 264/169 |
| 5,766,637 A * | 6/1998 | Shine et al. .................. 424/497 |
| 6,183,783 B1 * | 2/2001 | Benoit et al. ................ 424/497 |

OTHER PUBLICATIONS

Martin, J.W., "Shellac", Bradshaw–Praeger & Co. Chicago, Illinois, p. 442–464.
Merl, J.A. and Stock, K.W., "Silesia Confiserie Manual No. 4", Silesia Gerhard Hanke KG, Abt., Neuss Germany, 1996, p. 84.
Potter, C., "VOC Emission Limitations From Candy Manufacturing Facilities In California", Memorandum to Stephanie Smith, National Confectioner's Association, Mar. 22, 2000.
Stevens, J.P., "Assessment and Abatement of Volatile Organic Materials", Manufacturing Confectioner, Nov. 1999, p. 60–66.
Mitchell N.E., "The Clean Air Act Its Effect on Panning Candies", Manufacturing Confectioner, Oct. 1999, p. 41–44.
Giesecke, A., "Volatile Organic Compounds (VOCs)", Manufacturing Confectioner, Oct. 1999, p. 77–78.
Matson, D.W. and Petersen, R.C. and Smith, R.D., "Production of Powders and Films by the Rapid Expansion of Supercritical Solutions", Journal of Materials Science 22 (1987) p. 1919–1928.

\* cited by examiner

*Primary Examiner*—Carolyn Paden
(74) *Attorney, Agent, or Firm*—Anthony J. DeLaurentis PA

(57) ABSTRACT

A sprayable liquid coating composition, particularly for application to foodstuffs and pharmaceuticals, utilizes gaseous carbon dioxide to reduce the viscosity of a concentrated solution comprising an edible polymer and a solvent, such as ethyl alcohol or isopropyl alcohol. The addition of the gaseous carbon dioxide in the concentrated solution permits a sprayable composition to be produced using a significantly reduced level of solvent in the edible polymer/solvent solution. By reducing the amount of solvent used in the solution, the level of VOCs emission during the coating process also is reduced. Either supercritical carbon dioxide or subcritical carbon dioxide can be used as the gaseous carbon dioxide in the present invention.

25 Claims, 2 Drawing Sheets

COATING FOODS AND PHARMACEUTICALS WITH AN EDIBLE POLYMER USING CARBON DIOXIDE

RELATED APPLICATION

The present application claims priority from U.S. provisional application No. 60/228,966, filed Aug. 30, 2000, and provisional application No. 60/228,906 filed Aug. 29, 2000.

FIELD OF INVENTION

The present invention relates to a process of preparing a sprayable liquid coating composition wherein gaseous carbon dioxide is utilized to reduce the viscosity of a concentrated solution comprising an edible polymer and a solvent. The addition of the gaseous carbon dioxide in the concentrated solution permits a sprayable composition to be produced using a significantly reduced level of solvent in the edible polymer/solvent solution. Typical solvents used in the process have been deemed to be volatile organic compounds (VOCs). Thus, by reducing the amount of solvent used in the solution, the level of VOC emission during the coating process also is reduced. Either supercritical carbon dioxide or subcritical carbon dioxide can be used as the gaseous carbon dioxide in the present invention.

BACKGROUND OF THE INVENTION

It is well known to coat pharmaceutical and food products with an edible polymer in order to prevent degradation of the edible product, particularly degradation by moisture and/or oxidation. A number of edible polymers have been used in the prior art including for example shellac, cellulose derivatives, terpene resins and synthetic carboxylic polymers. These edible polymers are dispersed in a carrier or solvent and applied to the edible product by various means, such as panning, spraying, brushing or curtain coating.

The use of shellac as an edible polymer coating has increased in recent years.

Shellac is a naturally occurring resin of animal origin, derived from the seedlac of the tiny scale insect *Laccifer lacca*. Although the precise chemical nature of shellac has yet to be determined, it is the only known commercial resin of animal origin. Shellac's continued use as a resinous coating is due to its water resistant and lustrous finishing properties. Shellac can be manufactured by a solvent process to produce three types of shellac: dewaxed, dewaxed decolorized and wax-containing. For the wax-containing grade, raw seedlac and solvent, typically ethyl alcohol, are charged into a dissolving tank at a ratio of 1:4 by weight, refluxed and filtered. The wax content of these shellacs can be controlled using different proof alcohol to dissolve the lac. Dewaxed shellacs are made by dissolving seedlac in either (a) cooled alcohol of high proof or (b) weaker proof alcohol at slightly elevated temperature. Dewaxed decolorized shellac is produced in the same manner as the dewaxed shellacs followed by a treatment with activated carbon to remove the darker coloring material. Another type of shellac is bleached shellac which is produced from seedlac of Indian or Thailand origin. The seedlac is dissolved in an aqueous alkali solution, such as sodium carbonate, at a high temperature, and processed to remove impurities.

The versatility of shellac in coating compositions is demonstrated in its varied applications. It has been applied to wood, metal, glass fibers, foil, plastics, paper, ceramics, leather, rubber, hair, fruits, candy and tablet. In addition, shellac can be applied by any number of techniques, including brushing, rolling, doctoring, tumbling and spraying (Martin, J. W. "Shellac", Bradshaw-Praeger & Co. Chicago, Ill., p. 442–476). The viscosity of the shellac must be reduced in order to use it in a coating composition. Shellac generally is not water soluble, tending to form a colloidal dispersion. Thus, shellac typically is dissolved in a solvent, such as an alcohol, in order to reduce its viscosity. Current practices include dissolving from about 5 to 10 wt. % (Merl, J. A. and Stock, K. W., "Silesia Confiserie Manual No. 4", Silisia Gerhard Hanke KG, Abt., Neuss Germany, 1996, p. 84) to up to about 45 wt. % (Martin, J. W. "Shellac", Bradshaw-Praeger & Co. Chicago, Ill., p. 466–470) shellac in the solvent. More commonly, about 30 wt. % of shellac is dissolved in the solvent (Mitchell, N. E. "The Clean Air Act Its Effect on Panning Candies", Manufacturing Confectioner, October 1999, p. 41–44). Edible film coating compositions comprising an edible shellac dissolved in an alcohol-based solvent are described in U.S. Pat. No. 4,661,359 to Seaborne et al, issued Mar. 7, 1989, U.S. Pat. No. 4,710,228 to Seaborne, issued Oct. 16, 1985 and U.S. Pat. No. 4,810,534, issued Mar. 7, 1989.

One conventional process for coating edible products is panning. Panning involves tumbling the edible product (such as tablets, candies, etc.) in a revolving drum. As the product is tumbled, the edible shellac/alcohol solution is sprayed or ladled into the drum. Drying air is introduced to the pan in order to evaporate the alcohol, and the alcohol is exhausted into the air handling system and out of the factory. An example of such a process is disclosed in U.S. Pat. No. 3,949,096 to Johnson et al., issued Apr. 6, 1976, which describes an edible surface coating dispersion comprising an edible coating material and a fugitive solvent, wherein the solvent is volatized in a heating zone to leave a dry surface coating.

Ethyl and isopropyl alcohol are classified as a volatile organic compounds (VOCs) or volatile organic materials (VOMs). Volatile organic compounds are one cause of pollution, mostly in the form of ground level ozone, which is a highly reactive gas that can be harmful to the public and contribute to smog. Consequently, a serious drawback to the use of the shellac/alcohol coating solution is the emission of volatile organic compounds (VOCs). For example, a 55-gallon drum (about 400 pounds), of which 70% is ethanol, yields about 280 pounds of VOC fugitive emissions (Giesecke, A., "Volatile Organic Compounds (VOCs)", Manufacturing Confectioner, October 1998, p. 77–78).

The Environmental Protection Agency (EPA) has designated certain areas as "non-attainment areas" in order to regulate the amount of permissible VOC production for a given facility. There are several types of "non-attainment areas" including moderate, serious, severe and extreme; different rules regarding the level of permissible VOC emissions have been imposed for each area. For example, Chicago is classified as a severe non-attainment area. Chicago-area confectionary companies produce a significant portion of all panned candies sold in the United States. The process of pan-polishing of candies generally utilizes ethyl alcohol as the main solvent in the glaze, the ethyl alcohol being emitted into the atmosphere as a VOC in the absence of any controls. EPA restrictions now limit the VOC content of a glazing mixture to 3.5 lbs/gallon. If this limit cannot be achieved, control of at least 81% of the overall VOC emissions must be established. However, the currently available glazing systems and non-compliant glazing mixtures generate more than 5 lbs of potential VOCs/gallon (Mitchell, N. E. "The Clean Air Act Its Effect on Panning Candies", Manufacturing Confectioner, October 1999, p. 41–44).

Thus, in panning techniques where the solvent levels are too high, systems for capturing the solvent must be utilized. However, conventional panning emissions are fugitive VOC emissions that are not readily addressed by typical stack controls such as catalytic or thermal oxidizers or other available VOC reduction technologies (Potter, C., "*VOC Emission Limitations from Candy Manufacturing Facilities in California*", Memorandum to Stephanie Smith, National Confectioner's Association, Mar. 22, 2000). Therefore, "scrubbing" the exhaust stream in order to contain the VOCs is required, but it also is very cost prohibitive. As a result, there have been attempts to replace the alcohol with a substitute solvent, such as water or acetone. While acetone is legal in all states except California, the volatility of acetone as a substitute solvent makes it dangerous for use in panning operations. Water-soluble glazes also have been used as a substitute coating solution, but the production time is increased substantially due to increased drying time. In addition, the water-borne coatings are often susceptible to problems with humidity, such that the products begin to stick together.

Carbon dioxide specifically is excluded from the definition of VOCs (Stevens, J. P., "*Assessment and Abatement of Volatile Organic Materials*", Manufacturing Confectioner, November 1999, p. 60–66). Thus, the present invention contemplates the use of carbon dioxide as a viscosity reduction agent for an edible polymer suitable for use in a coating composition, thereby reducing or eliminating the required amount of solvent. U.S. Pat. No. 4,923,720 to Lee et al., issued May 8, 1990, provides a process and apparatus for using supercritical fluids, such as carbon dioxide, to reduce to application consistency viscous coatings in liquid spray applications. The Lee et al. patent generally discloses a process for a liquid spray application for coating a substrate comprising forming a liquid mixture from at least one polymeric compound capable of forming a coating on a substrate, at least one supercritical fluid, such as supercritical carbon dioxide, and optionally an active solvent, and then spraying the liquid mixture onto a substrate in the form of droplets having an average diameter of 1 micron or greater. The described process is cumbersome, including the requirement that the final liquid mixture be heated to avoid condensation of carbon dioxide and ambient water vapor prior to its introduction to the spray nozzle. The Lee et al. patent does not address using a supercritical fluid in the formation of edible coatings, nor does Lee et al. specifically provide for a reduction of volatile organic compounds (VOC) emissions. In addition, Lee et al. teaches away from the use of subcritical fluids, such as subcritical $CO_2$ in its liquid spray application.

Despite the advances of the prior art, a need still exists for a process and apparatus for coating foods with an edible polymer using gaseous carbon dioxide. Such a process and apparatus should lower significantly the amount of VOC emissions resulting from panning techniques of edible shellac solutions as imposed by the Clean Air Act of 1990. Such a process and apparatus also should provide an edible shellac solution that can be sprayed while using significantly lower amounts of VOCs. In addition, such as a process and apparatus should yield equal, if not improved, production rates, relative to processes and apparatus currently being used.

SUMMARY OF THE INVENTION

Accordingly, it is an object of the present invention to provide an edible sprayable liquid coating comprising a concentrated solution of an edible polymer and a solvent which is mixed with gaseous carbon dioxide.

It is also an object of the present invention to provide an edible sprayable liquid coating comprising a concentrated solution of edible shellac and an alcohol which is mixed with gaseous carbon dioxide.

It is another object of the present invention to provide an edible sprayable liquid coating which utilizes supercritical carbon dioxide or subcritical carbon dioxide in order to reduce the viscosity of the concentrated solution of edible polymer and solvent.

It is yet another object of the present invention to provide an edible sprayable liquid coating which can be applied onto confectionary and pharmaceutical tablets.

It is an additional object of the present invention to provide an edible sprayable liquid coating having a reduced amount of solvent in order to reduce volatile organic compound (VOC) emissions.

It is a further object of the present invention to provide a method of applying a sprayable liquid coating onto an edible substrate which reduces the amount of volatile organic compound (VOC) emissions.

It is still another object of the present invention to provide a method of applying a sprayable liquid coating onto an edible substrate which increases production rate.

It is an additional object of the present invention to provide a method of applying a sprayable liquid coating onto an edible substrate which reduces the risk of explosion.

It is another object of the present invention to provide an apparatus for producing a sprayable liquid coating from a concentrated solution of edible polymer and solvent which utilizes supercritical carbon dioxide.

It is also an object of the present invention to provide an apparatus for producing a sprayable liquid coating from a concentrated solution of edible polymer and solvent which utilizes subcritical carbon dioxide.

Additional objects, advantages and novel features of the invention will be set forth in part by the description and claims which follow, and in part will become apparent to those skilled in the art upon examination of the following specification or may be learned by practice of the invention.

These and other objects of the present invention are accomplished by providing a process of preparing a sprayable liquid coating wherein gaseous carbon dioxide is utilized to reduce the viscosity of a concentrated solution of an edible polymer and a solvent. In this manner, a sprayable composition is produced using a significantly reduced level of solvent in the solution, thereby significantly reducing the level of VOCs emissions during the coating process.

BRIEF DESCRIPTION OF THE DRAWINGS

The present invention will be better understood with reference to the appended drawing sheets, wherein.

DETAILED DESCRIPTION

Figure 1:
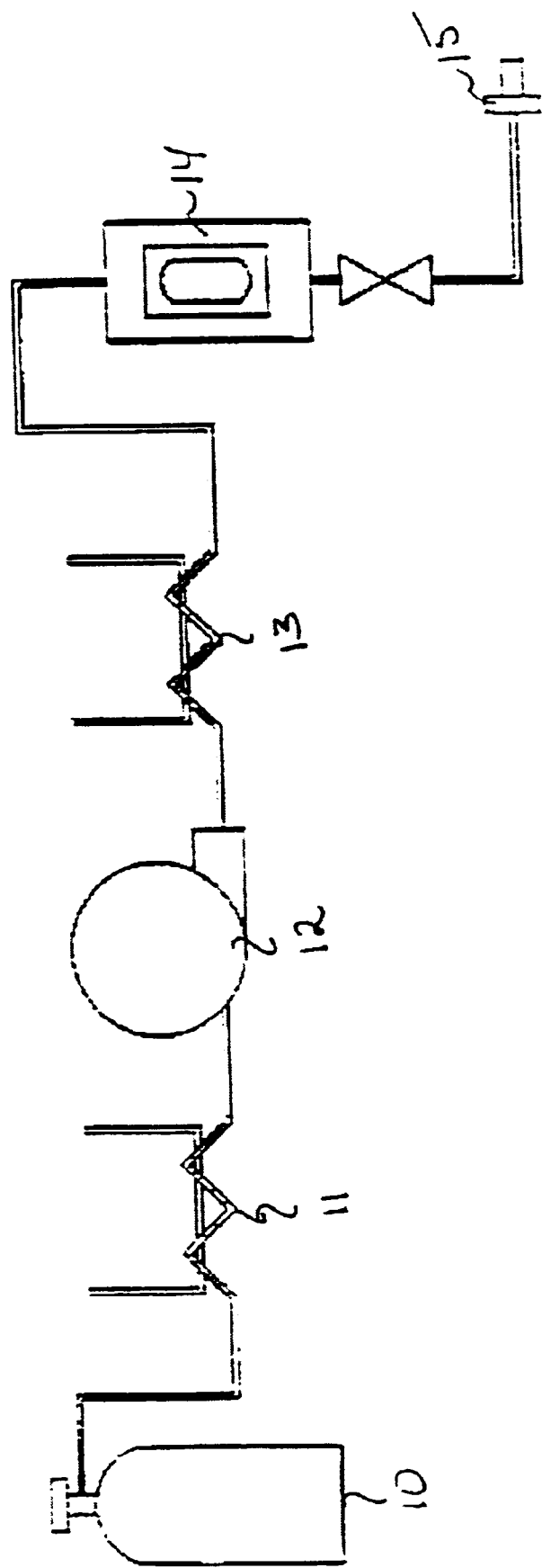
FIG. 1 is a schematic illustrating the process of the present invention, wherein supercritical carbon dioxide is used to reduce the viscosity of a concentrated solution of edible polymer and solvent.

The present invention relates to a method and apparatus for applying a sprayable liquid coating onto a substrate, in particular, an edible sprayable liquid coating for application onto a food or pharmaceutical item, including for example, sugar-panned confectionary or pharmaceutical tablets and compressed confectionary or pharmaceutical tablets. The sprayable liquid coating comprises a concentrated solution of an edible polymer and a solvent which is mixed with gaseous carbon dioxide. The gaseous carbon dioxide can be supercritical carbon dioxide or subcritical carbon dioxide. The gaseous carbon dioxide is utilized as a viscosity reducing agent and/or a propellant. Typically, to obtain an effective application, a liquid spray composition should have a viscosity of less than about 150 cps, preferably about 10 to about 100 cps and more preferably from about 20 to about 50 cps. The addition of carbon dioxide to the concentrated solution produces a sprayable liquid coating while also significantly reducing the amount of solvent required in the edible polymer/solvent solution.

Any type of edible polymer conventionally used in sprayable liquid coatings may be used in the present invention. Suitable edible polymers include, for example, edible shellac, such as orange, dewaxed, bleached or dewaxed and bleached shellacs. The concentrated solution comprises from about 45 to about 75 wt. % of the edible polymer, preferably from about 55 to about 65 wt. %. Suitable solvents for use in the concentrated solution include, for example, ethanol and isopropanol, in an amount of from about 25 to about 55 wt. %, preferably from about 35 to about 45 wt. %, based on the total weight of the concentrated solution. Suitable types of ethanol include anhydrous ethanol and the standard 190 proof ethanol (range 95–100% ethanol).

The amount of gaseous carbon dioxide in the sprayable liquid coating should be sufficient to provide the sprayable liquid coating with a viscosity suitable for spray coating, such as less than 150 cps. Preferably, the sprayable liquid coating composition has a viscosity of about 10 to about 100 cps, more preferably, from about 20 to about 50 cps. The sprayable liquid coating can be formed either by directly mixing the concentrated solution and gaseous carbon dioxide in a vessel and then transferring the sprayable liquid coating to a nozzle head or by mixing the concentrated solution and gaseous carbon dioxide within a spray nozzle. The nozzle head can be heated by any suitable means, including for example, by a resistive electric heater.

The sprayable liquid coating of the present invention optionally may comprise additional components well known in the edible coating field, including for example, pigments, flavorants, vitamins, drying agents, anti-bacterial agents, anti-skinning agents, plasticizers and preservatives.

The sprayable liquid coating can be prepared using either supercritical carbon dioxide or subcritical carbon dioxide. Supercritical carbon dioxide is $CO_2$ at a temperature and pressure above its critical point, that is, at a temperature above 31° C. and at a pressure greater than 1066 psi (73.8 atm or 7.3 MPa). When the pressure is high above the critical, the density of the supercritical $CO_2$ increases such that the supercritical $CO_2$ has some of the characteristics of a liquid. Subcritical carbon dioxide is $CO_2$ at a temperature above 31° C. and at a pressure below 1066 psi.

In a first embodiment, the sprayable liquid coating of the present invention is prepared utilizing supercritical carbon dioxide. Referring to FIG. 1, the carbon dioxide is fed from a siphon-fed tank 10 through a first heat exchanger 11 where it is chilled to a temperature of from about −20° C. to about 10° C. The chilled $CO_2$ then is conveyed to pump 12 where it is compressed to a supercritical pressure of from about 1060 psi to about 5000 psi. The compressed $CO_2$ is fed through a second heat exchanger 13 where it is heated to a temperature of from about 31° C. to about 90° C. and pumped to a high pressure vessel. 14. High pressure vessel 14 contains the concentrated solution of edible polymer and solvent (e.g. edible shellac and alcohol). The supercritical carbon dioxide is mixed with concentrated edible polymer/solvent solution for a period of time sufficient for the $CO_2$ to be dissolved within the solution. Preferably, the supercritical $CO_2$ is mixed with the concentrated solution for from about a few seconds to about a few minutes. More particularly, the supercritical $CO_2$ can be mixed with the concentrated solution for as little as about 1.0 seconds to about 20.0 minutes. Once the supercritical $CO_2$ has been dissolved within the concentrated solution, a sprayable liquid coating is produced which is transferred to an expansion nozzle 15 suitable for atomized spraying.

Figure 2:
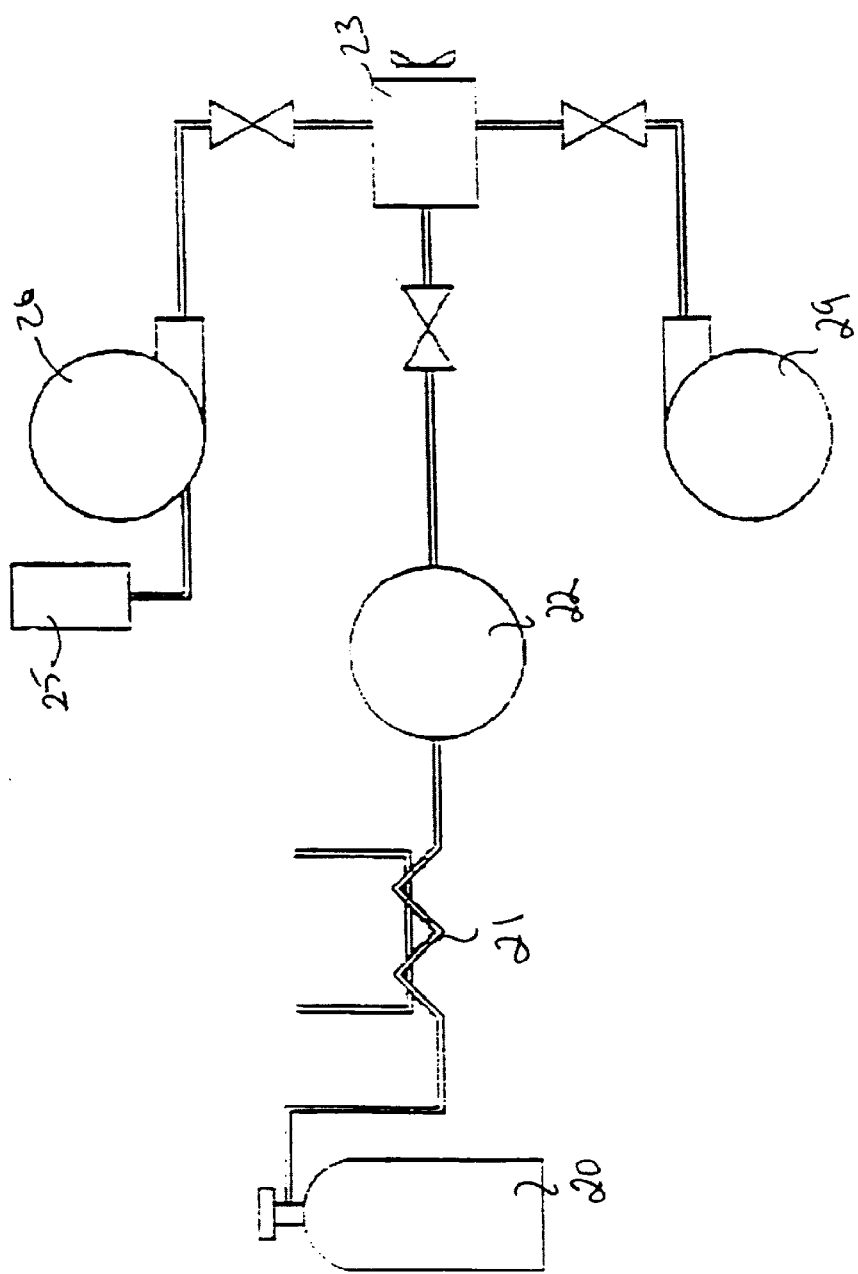
FIG. 2 is a schematic illustrating the process of the present invention, wherein subcritical carbon dioxide is used to reduce the viscosity of a concentrated solution of edible polymer and solvent.

In a second embodiment, the sprayable liquid coating of the present invention is prepared utilizing subcritical carbon dioxide. Referring to FIG. 2, the carbon dioxide is fed from a siphon-fed tank 20 through a heat exchanger 21 where the $CO_2$ is heated to a temperature of from about 20° C. to about 50° C. The heated subcritical $CO_2$ is passed through a forward pressure regulator 22 to regulates the pressure in the nozzle and released into a modified spray nozzle 23 typically used in panning operations. A concentrated solution of edible polymer and solvent is fed from a holding tank 25 to pump 26 and then pumped into the nozzle 23 where it is mixed with the subcritical $CO_2$ for a period of from about 1.0 seconds to about 3.0 seconds until the subcritical $CO_2$ has been dissolved within the concentrated solution to produce a sprayable liquid coating. Once the sprayable liquid coating is produced, it can be released through the nozzle 23 as an atomized spray. The sprayable liquid coating can be further atomized using compressed air from pump 29.

The following examples are intended to merely illustrate the invention, and it is to be understood the invention is not limited thereto.

EXAMPLE ONE

Supercritical $CO_2$

A concentrated solution of 50.0 ml of Dewaxed, Bleached Shellac and 100% pure Ethanol was prepared at a concentration of 50% Shellac and 50% Ethanol (by weight). The concentrated shellac/ethanol solution was placed in high pressure vessel that was maintained in an insulated box at 50° C. Liquid $CO_2$ was drawn from a siphon-fed tank and through a first heat exchanger. The $CO_2$ was chilled to 0° C. via a heat exchanger to maintain the $CO_2$ in a liquid state, a physical requirement of the pump. The $CO_2$ was pumped to a supercritical pressure of 1100 psi. The compressed $CO_2$ then was heated through a second heat exchanger to 50° C. and directed, as a supercritical fluid, to the high-pressure vessel. The supercritical fluid and concentrated solution were mixed for 30.0 seconds after the introduction of the supercritical $CO_2$ to form a liquid spray coating composition. The resulting liquid spray coating composition was released through an atomizing nozzle onto substrate targets placed 12" from the nozzle. Test observations revealed a sampling of spray droplets sufficiently small for a typical coating application.

EXAMPLE TWO

Supercritical $CO_2$

The second example is similar to the procedure for Example 1 except that the $CO_2$ pressure was increased to 3000 psi via the pump. The resulting liquid spray coating composition was released through the atomizing nozzle onto a substrate target. Test observations revealed that a sufficient atomization of the solution was achieved and sprayed.

EXAMPLE THREE

Supercritical $CO_2$

The third example illustrates the spraying of the liquid spray coating composition onto a sample of pharmaceutical tablets. Processing was once again configured as outlined in Example 1, except that the pressure of the $CO_2$ was increased to 2000 psi. The resulting liquid spray coating composition was sprayed onto a sample of 3 liters of Vitamin C Tablets (500 mg tablets). Test observations revealed that an acceptable, smooth coating of shellac was applied, indicating that the samples observed on substrate targets in Example One and Example Two provide a sufficiently atomized coating for atypical spray coating application.

EXAMPLE FOUR

Subcritical $CO_2$

A concentrated solution of 50 ml of Dewaxed, Bleached Shellac and 100% pure Ethanol was prepared at a concentration of 50% Shellac and 50% Ethanol (by weight). The concentrated shellac/ethanol solution was placed in holding tank. Liquid $CO_2$ was drawn from a siphon-fed tank through a heat exchanger. The $CO_2$ was heated to 20° C. via heat the exchanger and passed through a forward pressure regulator to an atomizing nozzle in order to maintain pressure within the nozzle at approximately 200 psi. The concentrated solution was pumped from the holding tank to the atomizing nozzle where mixing with the subcritical $CO_2$ occurred in order to form a liquid spray coating composition. After an approximate 1.0 to 2.0 second dwell time within the cavity of nozzle, the resulting liquid spray coating composition was released through the atomizing nozzle and onto substrate targets placed 12" from the nozzle. Test observations revealed a sampling of spray droplets sufficiently small for a typical coating application.

EXAMPLE FIVE

Subcritical $CO_2$

The example is similar to Example Four, except that the concentration solution was prepared at a concentration of 60% Shellac and 40% Ethanol (by weight). The nozzle pressure was raised via the forward pressure regulator to approximately 350 psi, and the $CO_2$ was heated to a temperature of 20° C. As in Example Four, test observations of substrate targets revealed that successful atomization and spraying of the solution was completed.

EXAMPLE SIX

Subcritical $CO_2$

This example is similar to Example Four, except that concentrated solution was prepared at a concentration of 65% Shellac and 35% Ethanol (by weight). Test observations revealed that atomization and spraying of the solution onto a sample target substrate was successfully conducted. This successful test demonstrates that the most significant test result with respect to VOC reduction, due to the high concentration of Shellac relative to Ethanol.

The foregoing examples demonstrate that a concentrated solution of shellac and solvent, suitable for use in a liquid spray coating composition, can be produced using significantly less solvent than the 30% shellac and 70% solvent ratio typically used in conventional panning techniques. The examples also demonstrate that significant reduction in solvent, and hence volatile organic compound, can be achieved through the use of either supercritical $CO_2$ or subcritical $CO_2$ to reduce the viscosity of the composition.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A method of applying a sprayable liquid coating onto an edible preformed solid substrate, which comprises:

(a) forming a concentrated solution comprising from about 45 to about 75 wt. % of an edible polymer and from about 25 to about 55 wt. % of a solvent, and transferring said concentrated solution to a high pressure vessel;

(b) chilling liquid carbon dioxide to a temperature of from about −20° C. to about 10° C.;

(e) compressing said chilled carbon dioxide to a supercritical pressure of from about 1060 psi to about 5000 psi;

(d) heating the supercritical carbon dioxide to a temperature of from about 31° C. to about 90° C.;

(e) transferring the heated supercritical carbon dioxide to said high pressure vessel;

(f) dissolving the heated supercritical carbon dioxide into said concentrated solution in said high pressure vessel in an amount sufficient to reduce the viscosity of the resulting solution to form a sprayable liquid coating composition, and (g) atomizing and spraying said sprayable liquid coating composition onto the surface of an edible preformed solid substrate such that, upon evaporation of said solvent and carbon dioxide from said sprayable liquid coating composition, the edible preformed solid substrate will have been coated with a solid edible surface coating.

2. The method in accordance with claim 1, wherein said edible polymer is selected from the group consisting of edible shellac, orange shellac, dewaxed shellac, bleached shellac, and dewaxed and bleached shellac.

3. The method in accordance with claim 1, wherein said solvent is selected from the group consisting of ethyl alcohol and isopropyl alcohol.

4. The method in accordance with claim 1, wherein said concentrated solution comprises from about 55 to about 65 wt. % of edible polymer and from about 35 to about 45 wt. % of solvent.

5. The method in accordance with claim 1, wherein the amount of supercritical carbon dioxide is sufficient to reduce the viscosity of the sprayable liquid coating composition to less than about 150 cps.

6. The method in accordance with claim 5, wherein the amount of supercritical carbon dioxide is sufficient to reduce the viscosity of the sprayable liquid coating composition to from about 10 to about 100 cps.

7. The method in accordance with claim 1, wherein said edible polymer is an edible shellac and said solvent is ethanol.

8. The method in accordance with claim 7, wherein said concentrated solution comprises from about 55 to about 65 wt. % of edible shellac and from about 35 to about 45 wt. % of ethanol.

9. The method in accordance with claim 7, wherein the amount of supercritical carbon dioxide is sufficient to reduce the viscosity of the sprayable liquid coating composition to less than about 150 cps.

10. The method in accordance with claim 1, wherein said preformed solid edible substrate provided in the form of edible tablets.

11. A method of applying a sprayable liquid coating composition onto an edible preformed solid substrate, which comprises:
  (a) forming a concentrated solution comprising from about 45 to about 75 wt. % of an edible polymer and from about 25 to about 55 wt. %;
  (b) heating gaseous carbon dioxide to a subcritical temperature of from about 20° C. to about 70° C.;
  (c) passing the heated subcritical carbon dioxide into a spray nozzle head;
  (d) transferring said concentrated solution to said spray nozzle head;
  (e) dissolving the subcritical carbon dioxide into said concentrated solution in said spray nozzle head in an amount sufficient to reduce the viscosity of the resulting solution to form a sprayable liquid coating composition, and
  (f) atomizing and spraying said sprayable liquid coating composition onto an edible preformed solid substrate such that, upon evaporation of said solvent and carbon dioxide from said sprayable liquid coating composition, the edible preformed solid substrate will have been coated with a solid edible surface coating.

12. The method in accordance with claim 11, wherein said edible polymer is selected from the group consisting of edible shellac, orange shellac, dewaxed shellac, bleached shellac, and dewaxed and bleached shellac.

13. The method in accordance with claim 11, wherein said solvent is selected from the group consisting of ethyl alcohol and isopropyl alcohol.

14. The method in accordance with claim 11, wherein said concentrated solution comprises from about 55 to about 65 wt. % of edible polymer and from about 35 to about 45 wt. % of solvent.

15. The method in accordance with claim 11, wherein the amount of supercritical carbon dioxide is sufficient to reduce the viscosity of the sprayable liquid coating composition to less than about 150 cps.

16. The method in accordance with claim 15, wherein the amount of supercritical carbon dioxide is sufficient to reduce the viscosity of the sprayable liquid coating composition to from about 10 to about 100 cps.

17. The method in accordance with claim 11, wherein said edible polymer is an edible shellac and said solvent is ethanol.

18. The method in accordance with claim 17, wherein said concentrated solution comprises from about 55 to about 65 wt. % of edible shellac and from about 35 to about 45 wt. % of ethanol.

19. The method in accordance with claim 17, wherein the amount of supercritical carbon dioxide is sufficient to reduce the viscosity of the sprayable liquid coating composition to less than about 150 cps.

20. The method in accordance with claim 11, wherein said edible preformed solid substrate provided in the form of edible tablets.

21. The method in accordance with claim 11, further comprising adding compressed air to said sprayable liquid coating composition.

22. The method in accordance with claim 11, wherein said spray nozzle head is heated.

23. A method of applying a sprayable liquid coating onto an edible preformed solid substrate, which comprises:
  (a) forming a concentrated solution solution comprising from about 45 to about 75 wt. % of an edible polymer and from about 25 to about 55 wt. % solvent, and transferring said concentrated solution to a high pressure vessel;
  (b) chilling liquid carbon dioxide;
  (c) compressing said chilled carbon dioxide to a supercritical pressure;
  (d) heating the supercritical carbon dioxide to a temperature of from about 31° C. to about 90° C.;
  (e) transferring the heated supercritical carbon dioxide to said high pressure vessel;
  (f) dissolving the heated supercritical carbon dioxide into said concentrated solution in said high pressure vessel in an amount sufficient to reduce the viscosity of the resulting solution to form a sprayable liquid coating composition, and
  (g) atomizing and spraying said sprayable liquid coating composition onto an edible preformed solid substrate such that, upon evaporation of said solvent and carbon dioxide from said sprayable liquid coating composition, the edible preformed solid substrate will have been coated with a solid edible surface coating.

24. A method of applying a sprayable liquid coating composition onto an edible preformed solid substrate, which comprises:
  (a) forming a concentrated solution comprising from about 45 to about 75 wt. % of an edible polymer and from about 25 to about 55 wt. % of a solvent;
  (b) passing heated subcritical carbon dioxide into a spray nozzle head;
  (c) transferring said concentrated solution to said spray nozzle head such that the combination of said concentrated solution and said carbon dioxide forms sprayable liquid coating composition having a viscosity which is reduced relative to the viscosity of said concentrated solution, and
  (d) atomizing and spraying said sprayable liquid coating composition onto an edible preformed solid substrate.

25. A sprayable liquid coating composition, which is formed by the following steps
  (a) forming a concentrated solution comprising from about 45 to about 75 wt. % of an edible polymer and from about 25 to about 55 wt. % of a solvent;
  (b) passing heated subcritical carbon dioxide into a spray nozzle head;
  (c) transferring said concentrated solution to said spray nozzle head; and
  (d) dissolving the subcritical carbon dioxide into said concentrated solution in said spray nozzle head in an amount sufficient to reduce the viscosity of the resulting solution to less than about 150 cps and to form a sprayable liquid coating composition.

* * * * *

UNITED STATES PATENT AND TRADEMARK OFFICE
CERTIFICATE OF CORRECTION

PATENT NO.     : 6,723,363 B2
DATED          : April 20, 2004
INVENTOR(S)    : Ziegler et al.

It is certified that error appears in the above-identified patent and that said Letters Patent is hereby corrected as shown below:

Column 1,
Line 10, after "RELATED APPLICATION", and before "FIELD OF INVENTION" insert the following:
-- GOVERNMENT SPONSORSHIP
    This invention was made with support from the Government under USDA Hatch Act Project No. PEN03591. The Government has certain rights in the invention. --

Signed and Sealed this

Twenty-second Day of February, 2005

JON W. DUDAS
*Director of the United States Patent and Trademark Office*